US011673854B2

United States Patent
Ludolph et al.

(10) Patent No.: US 11,673,854 B2
(45) Date of Patent: *Jun. 13, 2023

(54) ALKOXYLATED ESTERAMINES AND SALTS THEREOF

(71) Applicant: BASF SE, Ludwigshafen am Rhein (DE)

(72) Inventors: Bjoern Ludolph, Ludwigshafen am Rhein (DE); Sophia Ebert, Ludwigshafen am Rhein (DE); Christian Bittner, Ludwigshafen am Rhein (DE)

(73) Assignee: BASF SE

( * ) Notice: Subject to any disclaimer, the term of this patent is extended or adjusted under 35 U.S.C. 154(b) by 0 days.

This patent is subject to a terminal disclaimer.

(21) Appl. No.: 16/624,964

(22) PCT Filed: Jun. 26, 2018

(86) PCT No.: PCT/EP2018/067111
§ 371 (c)(1),
(2) Date: Dec. 20, 2019

(87) PCT Pub. No.: WO2019/007454
PCT Pub. Date: Jan. 10, 2019

(65) Prior Publication Data
US 2020/0140374 A1  May 7, 2020

(30) Foreign Application Priority Data

Jul. 7, 2017 (EP) .................................... 17180161

(51) Int. Cl.
*C07C 229/08* (2006.01)
*A61K 8/44* (2006.01)
*A61Q 5/02* (2006.01)
*A61Q 19/10* (2006.01)
*C07C 227/18* (2006.01)
(Continued)

(52) U.S. Cl.
CPC .............. *C07C 229/08* (2013.01); *A61K 8/41* (2013.01); *A61K 8/44* (2013.01); *A61Q 5/02* (2013.01); *A61Q 19/10* (2013.01); *C07C 227/18* (2013.01); *C08G 59/52* (2013.01); *C11D 3/33* (2013.01)

(58) Field of Classification Search
CPC ....... C07C 229/08; C07C 227/18; A61K 8/41; A61K 8/44; A61K 8/91; A61Q 19/10; A61Q 5/02; C08G 59/52; C08G 65/2609; C08G 65/33396; C11D 1/46; C11D 3/33; C11D 3/3723; B29D 2030/3228; B29D 2030/3242; B29D 2030/325; B29D 30/32; B29D 2030/2614; B29D 2030/2657; B29D 30/244; B29D 30/26; C22C 38/001; C22C 38/02; C22C 38/04; C22C 38/06; C22C 38/08; C22C 38/12; C22C 38/14;
(Continued)

(56) References Cited

U.S. PATENT DOCUMENTS 6,346,643 B1  2/2002  Lele et al.
8,735,332 B2  5/2014  Leinweber et al.
(Continued)

FOREIGN PATENT DOCUMENTS

CN  104645348  *  5/2015
CN  104645348 A    5/2015
(Continued)

OTHER PUBLICATIONS

JP2005263890 translated (Year: 2005).*
(Continued)

*Primary Examiner* — Yevgeny Valenrod
*Assistant Examiner* — Blaine G Doletski
(74) *Attorney, Agent, or Firm* — Faegre Drinker Biddle & Reath LLP

(57) ABSTRACT

The present invention relates to alkoxylated esteramines of Formula (I) and salts thereof. Esteramines according to the present invention may be used in cleaning composition, for example in liquid laundry detergents. They lead to improved cleaning performance of said compositions, for example when used in cold water washing conditions. They surprisingly boost grease cleaning performance of liquid laundry detergents, especially under cold water washing conditions. Whiteness is also improved. The esteramine according to the present invention show improved compatibility in liquid laundry detergent formulations.

10 Claims, No Drawings

(51) Int. Cl.
*C11D 3/33* (2006.01)
*A61K 8/41* (2006.01)
*C08G 59/52* (2006.01)

(58) Field of Classification Search
CPC ........ C21D 2211/005; C21D 2211/009; C21D 8/0226; C21D 9/46
See application file for complete search history.

(56) References Cited

U.S. PATENT DOCUMENTS

| | | | |
|---|---|---|---|
| 2010/0330004 | A1 | 12/2010 | Burgo |
| 2015/0273108 | A1 | 10/2015 | Askari et al. |

FOREIGN PATENT DOCUMENTS

| | | | |
|---|---|---|---|
| DE | 2025629 | A1 | 12/1971 |
| EA | 023366 | B1 | 5/2016 |
| EP | 2000460 | A1 | 12/2008 |
| EP | 2172508 | A1 | 4/2010 |
| EP | 2360203 | A1 | 8/2011 |
| JP | 2003064282 | A | 3/2003 |
| JP | 2005263890 | * | 9/2005 |
| JP | 2005263890 | A | 9/2005 |
| JP | 2014-062193 | A | 4/2014 |
| JP | 2014-070093 | A | 4/2014 |
| JP | 2015-516240 | A | 6/2015 |
| KR | 10-1710186 | B1 | 3/2017 |
| WO | WO-2003059317 | A2 | 7/2003 |
| WO | WO-2007054226 | A1 | 5/2007 |
| WO | 2014/158288 | A1 | 10/2014 |

OTHER PUBLICATIONS

U.S. Appl. No. 16/624,956, filed Dec. 20, 2019.
U.S. Appl. No. 62/529,510, filed Jul. 2017.
U.S. Appl. No. 62/594,599, filed Dec. 2017.
U.S. Appl. No. 62/529,511, filed Jul. 2017.
U.S. Appl. No. 62/594,606, filed Dec. 2017.
European Search Report for EP Patent Application No. 17180161.6, dated Jan. 24, 2018, 3 pages.
William Reusch, "Proteins, Peptides and Amino Acids", XP002777120, May 5, 2013, 10 pages.
International search Report for PCT/EP2018/067047 dated Sep. 27, 2018.
International Search Report for PCT/EP2018/067111 dated Oct. 1, 2018.
Written Opinion of the International Searching Authority for PCT/EP2018/067047 dated Sep. 27, 2018.
Written Opinion of the International Searching Authority for PCT/EP2018/067111 dated Oct. 1, 2018.
Flach, et al., "New insoluble surfactant systems as aids in catalysis. A convenient method for nonbonded immobilization of catalytically active transition metal complexes", Colloid and Polymer Science, vol. 274, Issue 3, Mar. 1996, pp. 261-268.
Boekhoven, et al., "Size control and compartmentalization in self-assembled nano-structures of a multisegment amphiphile", Chemical Communications, vol. 46, Issue 20, Apr. 7, 2010, pp. 3490-3492.
Osanai, et al., "Preparation and antimicrobial properties of polyoxyethylene monoalkyl ether glycinates and alaninates.", Effects of oxyethylene group on the antimicrobial properties, Bokin Bobai, vol. 15, Issue 4, 1987, pp. 157-162.

* cited by examiner

ALKOXYLATED ESTERAMINES AND SALTS THEREOF

CROSS-REFERENCE TO RELATED APPLICATIONS

This application is a national stage application (under 35 U.S.C. § 371) of PCT/EP2018/067111, filed Jun. 26, 2018, which claims benefit of European Application No. 17180161.6, filed Jul. 7, 2017, both of which are incorporated hereinby reference in their entirety.

The subject matter disclosed that was developed and the claimed invention was made by, or on behalf of, to a joint research agreement between BASF and Procter & Gamble that was in effect before the effective filing date of the claimed invention. The claimed invention was made as a result of activities undertaken within the scope of the joint research agreement.

The invention relates to alkoxylated esteramines and salts thereof.

Due to the increasing popularity of easy-care fabrics made of synthetic fibers as well as the increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, i.e. results comparable to those obtained with hot water washes, the demands on low temperature detergents are especially high.

It is known to include certain additives in detergent compositions to enhance the detergent power of conventional surfactants so as to improve the removal of grease stains at temperatures of 60° C. and below.

U.S. Pat. No. 6,346,643 discloses a process for the preparation of esters of poly(ethylene glycol) with amino acid hydrochlorides.

DE 2025629 discloses esters of glutamic acid and $C_{10}$ to $C_{18}$ fatty alcohols and derivatives.

WO 2007/054226 describes the use of pyroglutamic acid esters as gas hydrate inhibitors. The pyroglutamic acid esters are obtained by esterification of pyroglutamic acid or glutamic acid with an alcohol comprising 1 to 100 hydroxyl groups.

JP2003064282 discloses ligands for semiconductor particles based on triethylene glycol $C_1$ to $C_7$ monoethers esterified with $C_2$ to $C_{21}$ aminoacids.

JP2005263890 discloses esters of $C_6$ to $C_{10}$ ξ- to κ-amino acids of ethoxylated glycerols.

WO2003059317 describes polyethylene glyocol monomethyl or -ethyl ethers esterified with alpha-aminoacids as part of a medicinal aerosol composition.

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for amine compounds which provide grease removal abilities from fabrics and other soiled materials which at the same time do not negatively impact clay cleaning abilities or whiteness. There is a need for compounds having grease cleaning abilities at low temperatures.

It was an object of the present invention to provide compounds which comply with the above identifies objectives and needs.

This goal was achieved by the present invention as described herein below and as reflected in the claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Generally, as used herein, the term "obtainable by" means that corresponding products do not necessarily have to be produced (i.e. obtained) by the corresponding method or process described in the respective specific context, but also products are comprised which exhibit all features of a product produced (obtained) by said corresponding method or process, wherein said products were actually not produced (obtained) by such method or process. However, the term "obtainable by" also comprises the more limiting term "obtained by", i.e. products which were actually produced (obtained) by a method or process described in the respective specific context.

The present invention relates to alkoxylated esteramines of Formula (I) and salts thereof,

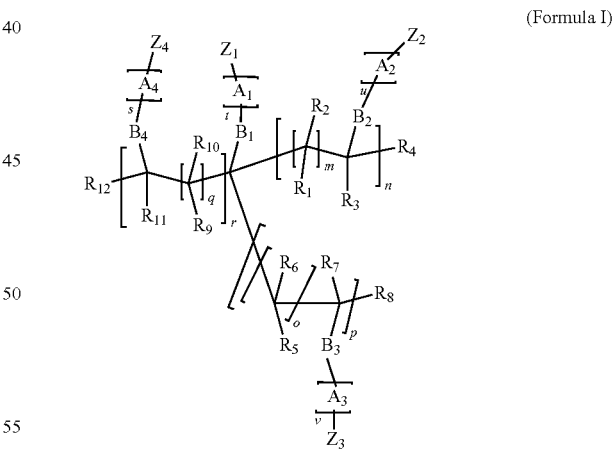

(Formula I)

wherein independently from each other n being an integer from 1 to 12, m being an integer for each repetition unit n independently selected from 0 to 12;

p being an integer from 0 to 12, o being an integer for each repetition unit p independently selected from 0 to 12;

r being an integer from 0 to 12, q being an integer for each repetition unit r independently selected from 0 to 12;

s being an integer from 0 to 100;
t being an integer from 1 to 100;
u being an integer from 0 to 100;
v being an integer from 0 to 100;
with the sum of s, t, u, and v being equal to or greater than 1;

$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein for s, t, u, and/or v equal to 1 the oxygen atom of the $A_1$, $A_2$, $A_3$, and $A_4$ group is bound to the B group and the following $A_1$, $A_2$, $A_3$, and $A_4$ groups are always bound via the oxygen atom to the previous $A_1$, $A_2$, $A_3$, and $A_4$ group.

$B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;

$R_4$, $R_5$, and $R_{12}$ being selected from the group consisting of H, linear alkyl, branched alkyl, and cycloalkyl;

$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the provisio that when p and r are both equal to 0, and n being at least 1, $Z_1$ and $Z_2$, are independently selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio that at least one substituent $Z_1$ and/or $Z_2$ is not OH, and with the provisio that $R_3$ contains equal to or more than 2 carbon atoms;

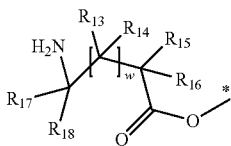
(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl;
ii) with the provisio that when n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio that at least one substituent $Z_1$, and/or $Z_2$, and/or $Z_3$, and/or $Z_4$, is not OH, and wherein for n and p equal to 1 and r equal to 0 at least one unit $A_1$, $A_2$, or $A_3$ is selected from the group consisting of 1,2-propyleneoxy group 1,2-1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

Esteramines according to the present invention may be used in cleaning composition, for example in liquid laundry detergents. They lead to improved cleaning performance of said compositions, for example when used in cold water washing conditions. They surprisingly boost grease cleaning performance of liquid laundry detergents, especially under cold water washing conditions. The esteramine according to the present invention show improved compatibility in liquid laundry detergent formulations.

In the following, the various embodiments of the present invention are described in more detail:

$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group pentenyloxy group, hexyloxy group, styryloxy group, decenyloxy group, dodecyloxy group, tetradecenyloxy group and hexadecenyloxy group, wherein for s, t, u, and/or v equal to 1 the oxygen atom of the $A_1$, $A_2$, $A_3$, and $A_4$ group is bound to the B group and the following $A_1$, $A_2$, $A_3$, and $A_4$ groups are always bound via the oxygen atom to the previous $A_1$, $A_2$, $A_3$, and $A_4$ group. When either of s, t, u, or v is equal to or more than 2, the independently selected $A_1$, $A_2$, $A_3$, and $A_4$ for each repetition unit s, t, u, or v either form a randomly distributed sidechain of various alkylenyloxy units for each sidechain s, t, u, or v, or the form a block structure with at least one alkylenyloxy group repeating itself at least two times, optionally followed by further blocks of different alkylenyloxy group repeating themselves at least two times.

In one embodiment $A_1$, $A_2$, $A_3$, and $A_4$ are independently from each other and independently for each repetition unit s, t, u, or v, selected from the list consisting of ethylenoxy group, 1,2-propyleneoxy group 1,2-1,2-propyleneoxy group, and 1,2-butylenoxy group. In another embodiment, $A_1$, $A_2$, $A_3$, and $A_4$ form each a block of at least two ethyleneoxy groups followed by a block of at least two propylenoxy groups, optionally followed by another block of at least two ethyleneoxy groups. In another embodiment, $A_1$, $A_2$, $A_3$, and $A_4$ form each a block of at least two 1,2-propyleneoxy groups followed by a block of at least two ethyleneoxy groups, optionally followed by another block of at least two 1,2-propyleneoxy group 1,2-1,2-propyleneoxy groups. In another embodiment, $A_1$, $A_2$, $A_3$, and $A_4$ are selected from the list consisting of ethyleneoxy group, 1,2-propyleneoxy group, and 1,2-butyleneoxy group in such a way that at least one block of ethyleneoxy groups, 1,2-propyleneoxy groups, or 1,2-butyleneoxy groups is formed, optionally followed by one or more blocks of ethyleneoxy groups, 1,2-propyleneoxy groups, or 1,2-butyleneoxy groups. In another embodiment, $A_1$, $A_2$, $A_3$, and $A_4$ are ethyleneoxy groups. In another embodiment, $A_1$, $A_2$, $A_3$, and $A_4$ are 1,2-propyleneoxy groups. In another embodiment, $A_1, A_2, A_3$, and $A_4$ are selected in such a way that at least for one of $A_1, A_2, A_3$, and $A_4$ a block of one to five ethyleneoxy groups is followed by a block of one to three propylenoxy groups followed by a block of one to five ethylenoxy groups.

In one embodiment, s, u, or v are each individually in the range of from 0 to 50 and t in the range of from 1 to 50. In another embodiment, s, u, or v are each individually in the range of from 0 to 20 and t in the range of from 1 to 20.

It is recognized that the alkoxylated esteramines of the present disclosure may be asymmetrically alkoxylated, meaning that the degree of alkoxylation may not be the same in each portion of the compound. Put another way, when at least two of s, t, u, and v are at least 1, the at least two of s, t, u, and v may not be equal to each other in a given compound.

In one embodiment of the present invention, $B_1, B_2, B_3$, and $B_4$ are independently from each other selected from the group consisting of a bond, and linear $C_1$ to $C_{12}$ alkanediyl groups. In another embodiment, $B_1, B_2, B_3$, and $B_4$ are independently from each other selected from the group consisting of a bond, and linear $C_1$ to $C_6$ alkanediyl groups. In another embodiment, $B_1, B_2, B_3$, and $B_4$ are independently from each other selected from the group consisting of a bond, and linear $C_1$ to $C_3$ alkanediyl groups. In another embodiment, $B_1, B_2, B_3$, and $B_4$ are independently from each other selected from the group consisting of a bond, and a $C_1$ alkanediyl group. In another embodiment $B_1, B_2, B_3$, and $B_4$ are all selected from the group consisting of a bond, and a $C_1$ alkanediyl group. In another embodiment $B_1, B_2, B_3$, and $B_4$ are all a bond.

In one embodiment of the present invention, $R_1, R_2, R_3, R_4, R_5, R_6, R_7, R_8, R_9, R_{10}, R_{11}$, and $R_{12}$ are all independently selected from the group consisting of H, linear alkyl, branched alkyl, and cycloalkyl. In one embodiment, $R_1, R_2, R_3, R_4, R_5, R_6, R_7, R_8, R_9, R_{10}, R_{11}$, and $R_{12}$ are all independently selected from the group consisting of H, linear $C_1$ to $C_{12}$ alkyl, and $C_1$ to $C_{12}$ branched alkyl. In another embodiment, $R_1, R_2, R_3, R_4, R_5, R_6, R_7, R_8, R_9, R_{10}, R_{11}$, and $R_{12}$ are all independently selected from the group consisting of H, linear $C_u$ to $C_6$ alkyl, and $C_1$ to $C_9$ branched alkyl.

For any one $Z_1, Z_2, Z_3$, and $Z_4$ being selected a compound according to Formula (II), said compound according to Formula (II) connects to the compound of Formula (I) via the bond labeled with *,

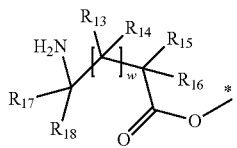

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}, R_{16}, R_{17}$, and $R_{18}$ being selected from the group consisting of H, linear alkyl, branched alkyl, and cycloalkyl. In one embodiment of the present invention, $R_{13}, R_{14}, R_{15}, R_{16}, R_{17}$, and $R_{18}$ are all independently selected from the group consisting of H, linear $C_1$ to $C_{12}$ alkyl, and $C_1$ to $C_{12}$ branched alkyl. In another embodiment, $R_{13}, R_{14}, R_{15}, R_{16}$, $R_{17}$, and $R_{18}$ are all independently selected from the group consisting of H, linear $C_1$ to $C_6$ alkyl, and $C_1$ to $C_9$ branched alkyl.

In one embodiment of the present invention, p and r are both equal to 0, and n being at least 1, $Z_1$ and $Z_2$, are independently selected from the group consisting of OH, alanine, glycine, lysine, and a compound according to Formula (II), wherein w is an integer in the range of from 1 to 4, wherein said compound according to Formula (II) connects to the compound according to Formula (I) via the bond labeled with *, with the provisio that at least one substituent $Z_1$ and/or $Z_2$ is not H, and with the provisio that $R_3$ contains equal to or more than 2 carbon atoms. In one embodiment of the present invention, p and r are both equal to 0, and n being at least 1, $Z_1$ and $Z_2$, are independently selected from the group consisting of alanine, a compound according to Formula (II), wherein w=0 and $R_{15}$ to $R_{18}$ are all H, a compound according to Formula (II), wherein w=1 and $R_{13}$ to $R_{18}$ are all H, and a compound according to Formula (II), wherein w=3 and $R_{13}$ to $R_{18}$ are all H, wherein said compound according to Formula (II) connects to the compound according to Formula (I) via the bond labeled with *, with the provisio that at least one substituent $Z_1$ and/or $Z_2$ is not H, and with the provisio that $R_3$ contains equal to or more than 2 carbon atoms.

In one embodiment of the present invention, p and r are both equal to 0, and n being 1, with m being in the range of from 0 to 10, with $R_8$ and $R_{12}$ being H. In another embodiment of the present invention, p and r are both equal to 0, and n being 1, with m being in the range of from 0 to 5, with $R_8$ and $R_{12}$ being H. In one embodiment, p and r are both equal to 0, and n being at least 1, wherein m is equal to 1 and $R_1$ and $R_2$ are both linear $C_2$ to $C_4$ alkyl groups. In another embodiment of the present invention, p and r are both equal to 0, and n being 1, with m being in the range of from 0 to 1, with $R_8$ and $R_{12}$ being H and $B_1$ and $B_2$ being bonds. In another embodiment of the present invention, p and r are both equal to 0, and n being 1, with m being 1, $R_3, R_4, R_8$ and $R_{12}$ being H, $R_1$ and $R_2$ being methyl, and $B_1$ and $B_2$ being bonds. In another embodiment of the present invention, p and r are both equal to 0, and n being 1, with m being 1, $R_3, R_4, R_8$ and $R_{12}$ being H, $R_1$ being butyl, $R_2$ being ethyl, and $B_1$ and $B_2$ being bonds. In another embodiment of the present invention, p and r are both equal to 0, and n being 1, with m being 1, $R_3, R_4, R_8$ and $R_{12}$ being H, $R_1$ being methyl, $R_2$ being propyl, and $B_1$ and $B_2$ being bonds. In another embodiment of the present invention, p and r are both equal to 0, and n being 1, with m being 1, $R_4$ being propyl, $R_3, R_8$ and $R_{12}$ being H, $R_1$ being H, $R_2$ being ethyl, and $B_1$ and $B_2$ being bonds. In another embodiment of the present invention, p and r are both equal to 0, and n being 5, with m being 0, with $R_1, R_2, R_4, R_8$ and $R_{12}$ being H and $B_1$ and $B_2$ being bonds.

In one embodiment of the present invention, p and r are both equal to 0, and n being 1, with m being in the range of from 0 to 10, with $R_8$ and $R_{12}$ being H, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups. In another embodiment of the present invention, p and r are both equal to 0, and n being 1, with m being in the range of from 0 to 5, with $R_8$ and $R_{12}$ being H, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups. In one embodiment, p and r are both equal to 0, and n being at least 1, wherein m is equal to 1 and $R_1$ and $R_2$ are both linear $C_2$ to $C_4$ alkyl groups, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups. In another embodiment of the present invention, p and r are both equal to 0, and n being 1, with m being in the range of from 0 to 1, with $R_8$ and $R_{12}$ being H, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups. In another embodiment of the present invention, p and r are both equal to 0, and n being 1, with m being 1, $R_3$, $R_4$, $R_8$ and $R_{12}$ being H, and $R_1$ and $R_2$ being methyl, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups. In another embodiment of the present invention, p and r are both equal to 0, and n being 1, with m being 1, $R_3$, $R_4$, $R_8$ and $R_{12}$ being H, and $R_1$ being butyl and $R_2$ being ethyl, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, and $B_1$ and $B_2$ being bonds. In another embodiment of the present invention, p and r are both equal to 0, and n being 1, with m being 1, $R_3$, $R_4$, $R_8$ and $R_{12}$ being H, and $R_1$ being methyl and $R_2$ being propyl, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, and $B_1$ and $B_2$ being bonds. In another embodiment of the present invention, p and r are both equal to 0, and n being 1, with m being 1, $R_3$, $R_4$, $R_8$ and $R_{12}$ being H, and $R_1$ being methyl and $R_2$ being propyl, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, and $B_1$ and $B_2$ being bonds. In another embodiment of the present invention, p and r are both equal to 0, and n being 1, with m being 1, $R_4$ being propyl, $R_3$, $R_8$ and $R_{12}$ being H, and $R_1$ being H and $R_2$ being ethyl, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, and $B_1$ and $B_2$ being bonds. In another embodiment of the present invention, p and r are both equal to 0, and n being 5, with m being 0, with $R_3$, $R_4$, $R_8$ and $R_{12}$ being H, t is of from 1 to 10, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, and $B_1$ and $B_2$ being bonds.

In one embodiment of the present invention n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, glycine, lysine and Formula (II), wherein w is an integer in the range of from 1 to 4, wherein Formula (II) connects to Formula (I) via the bond labeled with *, with the provisio that at least one substituent $Z_1$, and/or $Z_2$, and/or $Z_3$, and/or $Z_4$, is not OH. In another embodiment of the present invention n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of alanine, a compound according to Formula (II), wherein w=0 and $R_{15}$ to $R_{18}$ are all H, a compound according to Formula (II), wherein w=1 and $R_{13}$ to $R_{18}$ are all H, and a compound according to Formula (II), wherein w=3 and $R_{13}$ to $R_{18}$ are all H, wherein said compound according to Formula (II) connects to the compound according to Formula (I) via the bond labeled with *, and wherein for n and p equal to 1 and r equal to 0 at least one unit $A_1$, $A_2$, or $A_3$ is selected from the group consisting of 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group.

In one embodiment, n and p are both equal to 1, r is equal to 0, m and o are both equal to 0, $B_1$, $B_2$, and $B_3$ are equal to a chemical bond, $R_3$, $R_4$, $R_7$, $R_8$, and $R_{12}$ are all equal to H. In one embodiment, n and p are both equal to 1, r is equal to 0, m and o are both equal to 0, $B_1$, $B_2$, and $B_3$ are equal to methanediyl, $R_3$, $R_4$, $R_7$, and $R_8$, are all equal to H, and $R_{12}$ is equal to ethyl. In one embodiment, n and p are both equal to 1, r is equal to 0, m and o are equal to 0, $R_4$, $R_8$, and $R_{12}$ are equal to H. In one embodiment, n and p are both equal to 1, r is equal to 0, m and o are equal to 0, $R_4$, $R_8$, and $R_{12}$ are equal to H, and $B_1$, $B_2$, and $B_3$ are all bonds. In another embodiment, n and p are both equal to 1, r is equal to 0, m and o are equal to 1, $R_1$, $R_2$, $R_3$, $R_4$, $R_5$, $R_6$, $R_7$, and $R_8$ are all H, $R_{12}$ is ethyl, and $B_1$, $B_2$, and $B_3$ are all bonds. In another embodiment, n, p and r are all equal to 1, m, o, and q are 1, $R_1$, $R_2$, $R_3$, $R_4$, $R_5$, $R_6$, $R_7$, $R_8$, $R_9$, $R_{10}$, $R_{11}$, $R_{12}$ are all H, and $B_1$, $B_2$, $B_3$, and $B_4$ are all bonds.

In one embodiment, n and p are both equal to 1, r is equal to 0, m and o are both equal to 0, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, $A_3$ is for each repetition unit v selected from the group consisting of ethyleneoxy groups and 1,2-propyleneoxy groups, $B_1$, $B_2$, and $B_3$ are equal to a chemical bond, $R_3$, $R_4$, $R_7$, $R_8$, and $R_{12}$ are all equal to H. In one embodiment, n and p are both equal to 1, r is equal to 0, m and o are both equal to 0, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, $A_3$ is for each repetition unit v selected from the group consisting of ethyleneoxy groups and 1,2-propyleneoxy groups, $B_1$ is equal to methanediyl, $B_2$, and $B_3$ are equal to a chemical bond, $R_3$, $R_4$, $R_7$, and $R_8$, are all equal to H, and $R_{12}$ is equal to ethyl. In one embodiment, n and p are both equal to 1, r is equal to 0, m and o are equal to 0, $R_4$, $R_8$, and $R_{12}$ are equal to H. In one embodiment, n and p are both equal to 1, r is equal to 0, m and o are equal to 0, $R_4$, $R_8$, and $R_{12}$ are equal to H, $A_1$ is for each repetition unit t selected from the group consisting of ethyleneoxy groups and 1,2-propyleneoxy groups, u is of from 1 to 10, and $A_2$ is for each repetition unit u selected from the group consisting of ethyleneoxy groups and 1,2-propyleneoxy groups, $A_3$ is for each repetition unit v selected from the group consisting of ethyleneoxy groups and 1,2-propyleneoxy groups, and $B_1$, $B_2$, and $B_3$ are all bonds. In another embodiment, n and p are both equal to 1, r is equal to 0, m and o are equal to 1, $R_1$, $R_2$, $R_3$, $R_4$, $R_5$, $R_6$, $R_7$, and $R_8$ are all H, $R_{12}$ is ethyl, and $B_1$, $B_2$, and $B_3$ are all bonds. In another embodiment, n, p and r are all equal to 1, m, o, and q are 1, $R_1$, $R_2$, $R_3$, $R_4$, $R_5$, $R_6$, $R_7$, $R_8$, $R_9$, $R_{10}$, $R_{11}$, $R_{12}$ are all H, $A_1$ is for each repetition unit t selected from the group consisting of ethyleneoxy groups and 1,2-propyleneoxy groups, u is of from 1 to 10, $A_2$ is for each repetition unit u selected from the group consisting of ethyleneoxy groups and 1,2-propyleneoxy groups, $A_3$ is for each repetition unit v selected from the group consisting of ethyleneoxy groups and 1,2-propyleneoxy groups, $A_4$ is for each repetition unit s selected from the group consisting of ethyleneoxy groups and 1,2-propyleneoxy groups, and $B_1$, $B_2$, $B_3$, and $B_4$ are all bonds.

The esteramines according to the present invention are obtained either as free amines, as salts thereof or as a mixture of free amines and salts. Salts are formed by at least partial protonation of the amine groups by an acid being a protic organic acid or a protic inorganic acid. In one embodiment, the acid for at least partial protonation of the amine groups is selected from the group consisting of methanesulfonic acid, hydrochloric acid, hydrobromic acid, sulfuric acid, phosphoric acid, citric acid, and lactic acid. In one embodiment, the acid is selected from the group of methanesulfonic acid, hydrochloric acid, and sulfuric acid. In another embodiment, the acid is methanesulfonic acid.

Partial protonation in one embodiment is protonation of the amine groups in the range of from 1 to 99 mol-% of all amine groups, in another embodiment in the range of from 10 to 90 mol-% of all amine groups, in another embodiment in the range of from 25 to 85 mol-%, in another embodiment in the range of from 40 to 75 mol-% of all amine groups.

The present invention also comprises combinations of at least two embodiments as presented herein.

The present invention also relates to a process for preparation of esteramine or salt thereof comprises the steps of
a) Alkoxylation of an alcohol of Formula (III)

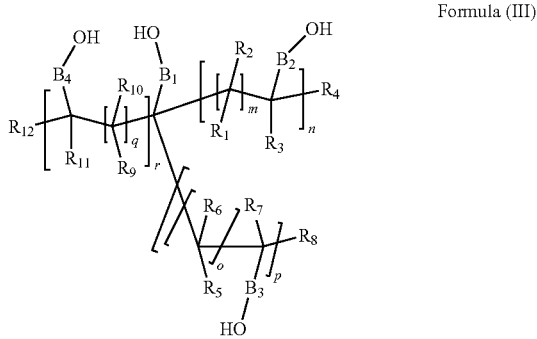

Formula (III)

wherein independently from each other
n being an integer from 1 to 12,
m being an integer for each repetition unit n independently selected from 0 to 12;
p being an integer from 0 to 12,
o being an integer for each repetition unit p independently selected from 0 to 12;
r being an integer from 0 to 12,
q being an integer for each repetition unit r independently selected from 0 to 12;
$B_1$, $B_2$, $B_3$, and $B_4$ are independently from each other selected from the group consisting of a bond, linear $C_1$ to $C_{12}$ alkanediyl groups, and branched $C_1$ to $C_{12}$ alkanediyl groups;
$R_4$, $R_8$, and $R_{12}$ being selected from the group consisting of H, linear alkyl, branched alkyl, and cycloalkyl;
$R_1$, $R_2$, and $R_3$ being independently for each repetition unit m of each repetition unit n being selected from the group consisting of H, linear alkyl, branched alkyl, and cycloalkyl;
$R_5$, $R_6$, and $R_7$ being independently for each repetition unit o of each repetition unit p being selected from the group consisting of H, linear alkyl, branched alkyl, and cycloalkyl;
$R_9$, $R_{10}$, and $R_{11}$ being independently for each repetition unit q of each repetition unit r being selected from the group consisting of H, linear alkyl, branched alkyl, and cycloalkyl;
with one or more $C_2$ to $C_{16}$ alkylene oxide, followed by
b) at least partial esterification of the alkoxylated alcohol with at least one acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and acids of Formula (IV)

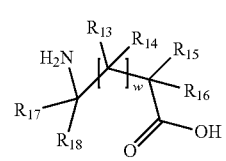

(Formula IV)

with w being an integer from 0 to 12,
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl.

In one embodiment of the present invention, $B_1$, $B_2$, $B_3$, and $B_4$ are independently from each other selected from the group consisting of a bond, and linear $C_1$ to $C_{12}$ alkanediyl groups. In another embodiment, $B_1$, $B_2$, $B_3$, and $B_4$ are independently from each other selected from the group consisting of a bond, and linear $C_1$ to $C_6$ alkanediyl groups. In another embodiment, $B_1$, $B_2$, $B_3$, and $B_4$ are independently from each other selected from the group consisting of a bond, and linear $C_1$ to $C_3$ alkanediyl groups. In another embodiment, $B_1$, $B_2$, $B_3$, and $B_4$ are independently from each other selected from the group consisting of a bond, and a $C_1$ alkanediyl group. In another embodiment $B_1$, $B_2$, $B_3$, and $B_4$ are all selected from the group consisting of a bond, and a $C_1$ alkanediyl group. In another embodiment $B_1$, $B_2$, $B_3$, and $B_4$ are all a bond.

In one embodiment of the present invention, $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear alkyl, branched alkyl, and cycloalkyl. In one embodiment, $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear $C_1$ to $C_{12}$ alkyl, and $C_1$ to $C_{12}$ branched alkyl. In another embodiment, $R_1$, $R_2$, $R_3$, $R_4$, $R_5$, $R_6$, $R_7$, $R_8$, $R_9$, $R_{10}$, $R_{11}$, and $R_{12}$ are all independently selected from the group consisting of H, linear $C_1$ to $C_6$ alkyl, and $C_1$ to $C_9$ branched alkyl.

Step a) Alkoxylation of alcohol according to Formula (III) with at least one $C_2$- to $C_{16}$-akylene oxide.

The alcohol of Formula (III) may be reacted with one single $C_2$- to $C_{16}$-alkylene oxide or combinations of two or more different $C_2$- to $C_{16}$-alkylene oxides. Using two or more different $C_2$- to $C_{16}$-alkylene oxides, the resulting polymer can be obtained as a block-wise structure or a random structure.

The molar ratio of alcohol of Formula (III) to total alkylene oxide may be in the range of from 1:1 to 1:400. In one embodiment, the molar ratio of the moles of hydroxyl groups of the alcohol of Formula (III) to the alkylene oxides with which the alkoxylation reaction is carried out may lie in the range of 1:1 to 1:100. In another embodiment the ratio of the moles of hydroxyl groups of the alcohol of Formula (III) to the alkylene oxides at which the alkoxylation reaction is carried out may lie in the range of from 1:2 to 1:50, in another embodiment in the range of 1:3 to 1:10.

This reaction may be undertaken generally in the presence of a catalyst at a reaction temperature from about 70 to about 200° C., in another embodiment from about 80 to about 160° C. This reaction may be affected at a pressure of up to about 10 bar, in another embodiment at a pressure of up to about 8 bar.

Examples of suitable catalysts comprise basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. In one embodiment, alkali metal hydroxides are used. In another embodiment, potassium hydroxide and sodium hydroxide are used. Typical use amounts for the base are from 0.01 to 10% by weight, in particular from 0.05 to 2% by weight, based on the total amount of alcohol and $C_2$- to $C_{16}$-alkylene oxide.

Step b) Esterification

The esterification reaction may be performed as known in the art. An inorganic or organic protic acid may be added to the product of step a). The molar ratio of amino acid to hydroxyl groups of the alkoxylated alcohol of step a) is 0.8:1 to 1:1.5. In one embodiment, the process is carried out with the molar ratio of the acid to the hydroxyl groups of the alkoxylated alcohol of step a) is in the range of from 0.1:1 to 1:1. Reaction temperatures may be from 50° C. to 200° C., in another embodiment from 80° C. to 160° C. The reaction may be affected by applying vacuum from 1000 mbar to 1 mbar, in another embodiment from 500 mbar to 5 mbar. Reaction times may be from 2 to 48 hours. Suitable solvents for the reaction may be water, toluene, xylene.

The effects for laundry as described and exemplified herein may be extrapolated to personal care applications.

The esteramines and salts thereof can be used in applications in personal care, as curing agent for epoxy resins, as reactant in the production of polymers, in polyurethanes, polyureas, and as thermoplastic polyamide adhesives. The can also be used in shampoo and body wash formulations. The esteramines and salts thereof may be included in personal care composition.

Methods $^1$H NMR measured in MeOD with Bruker Avance 400 MHz spectrometer.

pH is measured in 10% aqueous solution.

Hydroxyl values are measured according to DIN 53240-1.

Molecular weight of polyalkylene oxides (e.g. polyethylene glycol) is calculated from the measured hydroxyl values by following formula:

Molecular weight [g/mol]=1000/(hydroxyl value [mgKOH/g]/56.11)×hydroxyl groups per molecule

EXAMPLES

Comparative Example 1: Butyltriglycol Ester with 6-amino Hexane Acid, Methane Sulfonic Acid Salt In a 4-neck vessel with thermometer, reflux condenser, nitrogen inlet, dropping funnel, and stirrer, 64.39 g butyltriglycol and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 13.5 hours at 130° C. 122.0 g of a light brown solid is obtained. $^1$H-NMR in MeOD indicates complete conversion to 6-amino hexane acid acid-butyltriglycol ester as methane sulfonic acid salt.

Comparative Example 2: Polyethylene Glycol, $M_w$ Approx. 200 g/Mol; Ester with 6-amino Hexane Acid, Methane Sulfonic Acid Salt In a 4-neck vessel with thermometer, reflux condenser, nitrogen inlet, dropping funnel, and stirrer, 30.0 g polyethylene glycol ($M_w$ approx. 200 g/mol) and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 22 hours at 135° C. 97.0 g of a light brown solid is obtained. $^1$H-NMR in MeOD indicates complete conversion to 6-amino hexane acid acid polyethylene glycol ester as methane sulfonic acid salt.

Example 1 Use as Additives in Detergents

Technical stain swatches of blue knitted cotton containing Bacon Grease were purchased from Warwick Equest Ltd. The stains were washed for 30 min in a launder-o-meter (manufactured by SDL Atlas) at room temperature using per canister 500 mL of washing solution, 20 metal balls and ballast fabrics. The washing solution contained 5000 ppm of detergent composition DC1 (table 1). Water hardness was 2.5 mM ($Ca^{2+}$:$Mg^{2+}$ was 4:1). Additives were added to the washing solution of each canister separately and in the amount as detailed below. After addition the pH value was re-adjusted to the pH value of washing solution without additive.

Standard colorimetric measurement was used to obtain L*, a* and b* values for each stain before and after the washing. From L*, a* and b* values the stain level were calculated as color difference ΔE (calculated according to DIN EN ISO 11664-4) between stain and untreated fabric. Stain removal from the swatches was calculated as follows:

$$\text{Stain Removal Index} (SRI) = \frac{\Delta E_{initial} - \Delta E_{washed}}{\Delta E_{initial}} \times 100$$

$\Delta E_{initial}$=Stain level before washing $\Delta E_{washed}$=Stain level after washing Stain level corresponds to the amount of grease on the fabric. The stain level of the fabric before the washing ($\Delta E_{initial}$) is high, in the washing process stains are removed and the stain level after is smaller ($\Delta E_{washed}$) The better the stains have been removed the lower the value for $\Delta E_{washed}$ will be and the higher the difference will be to $\Delta E_{initial}$. Therefore, the value of stain removal index increases with better washing performance.

The esteramines according to the present invention can be used in the detergent composition of Table 1.

TABLE 1

| Detergent composition DC1 | |
| --- | --- |
| Ingredients of liquid detergent composition DC1 | percentage by weight |
| n-$C_{10}$-$C_{13}$-alkylbenzene sulfonic acid | 5.3 |
| coconut $C_{12}$-$C_{18}$ fatty acid | 2.4 |
| sodium laureth sulfate + 2 EO | 7.7 |
| potassium hydroxide | 2.2 |
| C13C15- oxo alcohol + 7 EO | 5.4 |
| 1,2 propylene glycol | 6 |
| ethanol | 2 |
| water | To Balance |
| pH of detergent composition DC1 = 8.0 | |

Example 2: Sorbitol, Propoxylated with 12 Mole Propylene Oxide, Ester with 2 Mole 6-aminohexane Acid, Methane Sulfonic Acid Salt 2a Sorbitol, Propoxylated with 12 Mole Propylene Oxide:

In a 2 l autoclave 278.85 g sorbitol and 2.65 g potassium tert-butylate are placed and the mixture is heated to 140° C. The vessel is purged three times with nitrogen and 1005.4 g propylene oxide is added in portions within 15 h. To complete the reaction, the mixture was allowed to post-react for additional 5 h at 140° C. The reaction mixture is stripped with nitrogen and volatile compounds are removed in vacuo at 80° C. After filtration 1325.0 g of a light yellowish oil is obtained (hydroxy value: 375 mgKOH/g).

2b Sorbitol, Propoxylated with 12 Mole Propylene Oxide, Ester with 2 Mole 6-aminohexane Acid, Methane Sulfonic Acid Salt In a 4-neck vessel with thermometer, nitrogen inlet, dropping funnel, and stirrer 88.14 g sorbitol propoxylated with 12 mole propylene oxide and 26.0 g 6-amino hexane acid are placed. The mixture is heated to 50° C., and 19.6 g methane sulfonic acid is added within 10 minutes under a constant stream of nitrogen. The temperature is allowed to rise to 60° C. during the addition. The reaction mixture is heated to 135° C. and is stirred for 4 hours at 135° C. Vacuum (5 mbar) is applied and the reaction mixture is stirred for additional 11.0 hours at 130° C. 121.0 g of a brown solid is obtained. $^1$H-NMR in MeOD indicates 33% conversion of hydroxyl groups into esterified hydroxyl groups.

Example 3 Sorbitol, Alkoxylated with 18 Mole Ethylene Oxide and 6 Mole Propylene Oxide, Ester with 2 Mole 6-aminohexane Acid, Methane Sulfonic Acid Salt 3a Sorbitol, Alkoxylated with 18 Mole Ethylene Oxide and 6 Mole Propylene Oxide In a 2 l autoclave 148.7 g sorbitol and 2.1 g potassium tert.-butylate are placed and the mixture is heated to 130° C. The vessel is purged three times with nitrogen and 634.3 g ethylene oxide is added within 20 h. The mixture is stirred for additional 5 h, followed by the addition of 278.8 g propylene oxide in portions within 10 h. To complete the reaction, the mixture is allowed to post-react for additional 5 h at 130° C. The reaction mixture was stripped with nitrogen and volatile compounds were removed in vacuo at 80° C. After filtration 1060.0 g of a light yellowish oil was obtained (hydroxy value: 250 mgKOH/g).

3b Sorbitol, Alkoxylated with 18 Mole Ethylene Oxide and 6 Mole Propylene Oxide, Ester with 6 Mole DL-Alanine, Methane Sulfonic Acid Salt In a 4-neck vessel with thermometer, nitrogen inlet, dropping funnel, and stirrer 105.8 g sorbitol, alkoxylated with 18 mole ethylene oxide and 6 mole propylene oxide and 42.8 g DL-alanine are placed. The mixture is heated to 50° C., and 47.1 g methane sulfonic acid is added within 10 minutes under a constant stream of nitrogen. The temperature is allowed to rise to 60° C. during the addition. The reaction mixture is heated to 135° C. and is stirred for 13 hours at 135° C. 186.0 g of a brown solid is obtained. $^1$H-NMR in MeOD indicates 100% conversion of hydroxyl groups into esterified hydroxyl groups.

Use as Additives in Detergents

Technical stain wfk20D (polyester/cotton 65/35, soil: pigment/sebum) from wfk Testgewebe GmbH, was used. Washing procedure and determination of stain removal index was followed as described above but with 1584 ppm of detergent composition 2 (table 2). The pH of the washing solution prior to washing with and without additives was adjusted in each case to pH=8.0.

TABLE 2

| Detergent composition DC2 | |
| --- | --- |
| Ingredients of liquid detergent composition DC2 | percentage by weight |
| linear $C_{11.8}$-alkylbenzene sulfonic acid | 17.6 |
| C12-C15 alkyl ethoxy (1.8) sulfate | 4.4 |
| C12-C14 alcohol + 9 ethylene oxide | 0.9 |
| C12-C18 fatty acid | 1.1 |
| C12-C14 amine oxide | 0.8 |
| chelant | 2.8 |
| solvent | 14.8 |
| brightener | 0.2 |
| sodium hydroxide | 1.9 |
| water | To Balance |
| Experiment 1 | SRI, wfk 20D |
| Without additive | 40.3 |
| Example 3: Sorbitol ethoxylated and propoxylated, ester with alanine, methane sulfonic acid salt; 0.024 g per wash | 45.5 |
| Experiment 2 | SRI, wfk 20D |
| Without additive | 42.4 |
| Example 2: Sorbitol propoxylated, ester with ester with 6-amino hexane acid, methane sulfonic acid salt; 0.024 g per wash | 47.1 |

The invention claimed is:

1. An esteramine of Formula (I) or salt thereof,

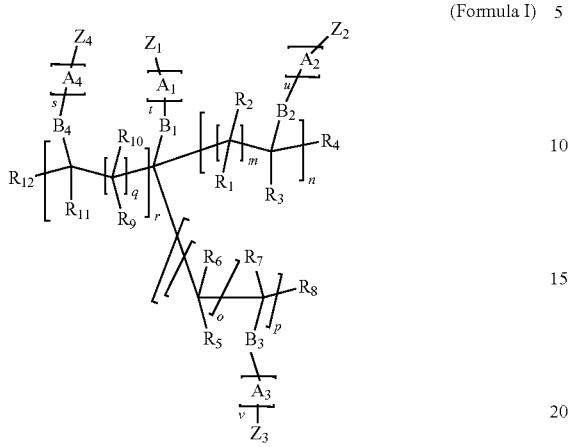

(Formula I)

wherein independently from each other
n being an integer from 1 to 12;
m being an integer for each repetition unit n independently selected from 0 to 12;
p is 0;
o being an integer for each repetition unit p independently selected from 0 to 12;
r is 0;
q being an integer for each repetition unit r independently selected from 0 to 12;
s being an integer from 0 to 100;
t being an integer from 1 to 100;
u being an integer from 0 to 100;
v being an integer from 0 to 100;
$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;
$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;
$R_4$, $R_8$, and $R_{12}$ being selected from the group consisting of H, linear alkyl, branched alkyl, and cycloalkyl;
$R_1$, $R_2$, and $R_3$ being independently for each repetition unit m of each repetition unit n being selected from the group consisting of H, linear alkyl, branched alkyl, and cycloalkyl;
$R_5$, $R_6$, and $R_7$ being independently for each repetition unit o of each repetition unit p being selected from the group consisting of H, linear alkyl, branched alkyl, and cycloalkyl;
$R_9$, $R_{10}$, and $R_{11}$ being independently for each repetition unit q of each repetition unit r being selected from the group consisting of H, linear alkyl, branched alkyl, and cycloalkyl;
with the proviso that $Z_1$ and $Z_2$, are independently selected from the group consisting of OH, alanine, glycine, lysine, and a compound according to Formula (II), wherein w is an integer in the range of from 1 to 4, wherein the compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms

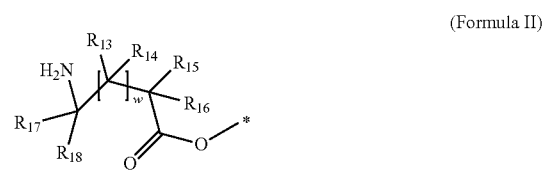

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl; and
$R_{15}$, $R_{16}$, $R_{17}$, and $R_{18}$ being selected from the group consisting of H, linear alkyl, branched alkyl, and cycloalkyl,
wherein
the esteramine is obtained by the process comprising the steps of
a) reacting an alcohol according to Formula (III)

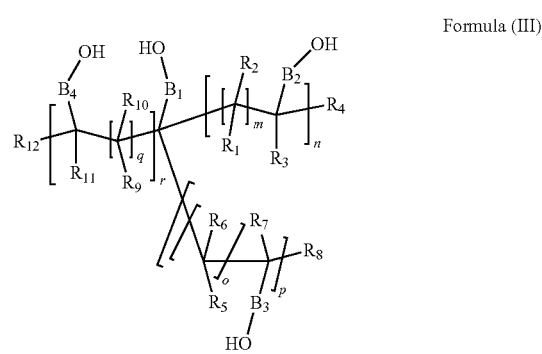

Formula (III)

wherein independently from each other
n, m, p, o, r and q, are defined above,
$B_1$, $B_2$, $B_3$, $B_4$, $R_1$, $R_2$, $R_3$ $R_4$, $R_5$, $R_6$, $R_7$, $R_8$, $R_9$, $R_{10}$, $R_{11}$, and $R_{12}$ are defined above,
with one or more $C_2$ to $C_{16}$ alkylene oxide, followed by
b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

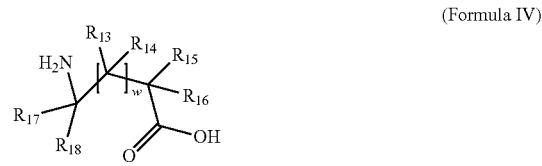

(Formula IV)

with w being an integer from 0 to 12, $R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

2. An esteramine of Formula (I) or salt thereof,

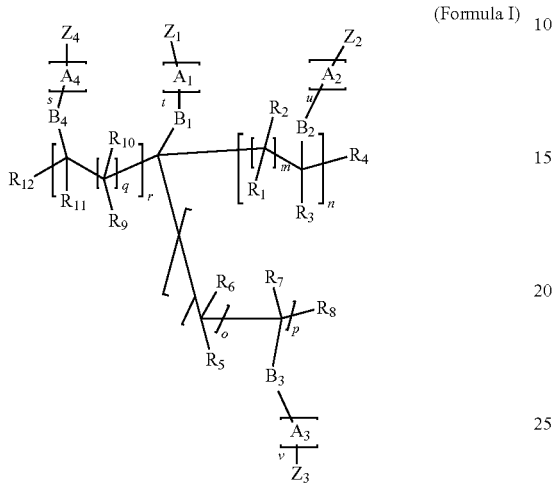

(Formula I)

wherein independently from each other n being an integer from 1 to 12;

m is 1;

p is 0;

o being an integer for each repetition unit p independently selected from 0 to 12;

r is 0;

q being an integer for each repetition unit r independently selected from 0 to 12;

s being an integer from 0 to 100;

t being an integer from 1 to 100;

u being an integer from 0 to 100;

v being an integer from 0 to 100;

$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;

$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_3$ for each repetition unit m of each repetition unit n being selected from the group consisting of H, linear alkyl, branched alkyl, and cycloalkyl;

$R_1$ and $R_2$ are both linear $C_2$ to $C_4$ alkyl groups;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

with the proviso that when p and r are both equal to 0, and n being at least 1, $Z_1$ and $Z_2$, are independently selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso that at least one substituent $Z_1$ and/or $Z_2$ is not OH, and with the proviso that R3 contains equal to or more than 2 carbon atoms;

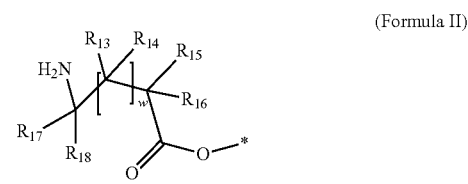

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl;

wherein the esteramine is obtained by the process comprising the steps of a) reacting an alcohol according to Formula (III)

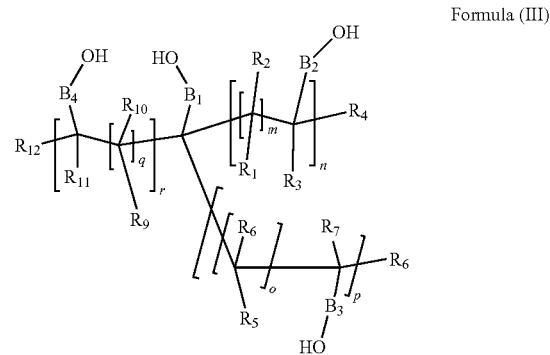

Formula (III)

wherein independently from each other n, m, p, o, r and q, are defined above;

$B_1$, $B_2$, $B_3$, $B_4$, $R_1$, $R_2$, $R_3$, $R_4$, $R_5$, $R_6$, $R_7$, $R_8$, $R_9$, $R_{10}$, $R_{11}$ and $R_{12}$ are defined above;

with one or more $C_2$ to $C_{16}$ alkylene oxide, followed by b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

19

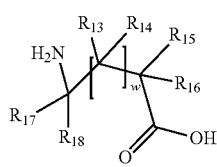

(Formula IV)

with w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

3. An esteramine of Formula (I) or salt thereof,

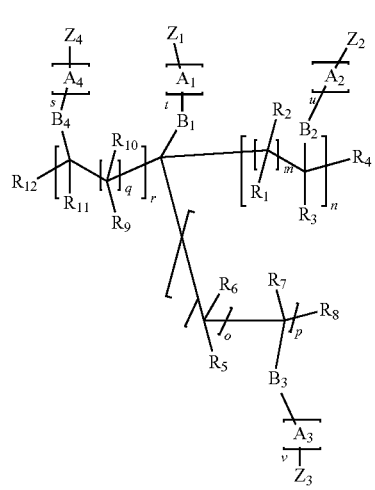

(Formula I)

wherein independently from each other r is 0 or 1;

p is 1 to 3;

n is 1 to 5;

m being an integer for each repetition unit n independently selected from 0 to 12;

q being an integer for each repetition unit r independently selected from 0 to 12;

s being an integer from 0 to 100;

t being an integer from 1 to 100;

u being an integer from 0 to 100;

v being an integer from 0 to 100;

$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;

$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

20

$R_3$ for each repetition unit m of each repetition unit n being selected from the group consisting of H, linear alkyl, branched alkyl, and cycloalkyl;

$R_1$ and $R_2$ are both linear $C_2$ to $C_4$ alkyl groups;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

when n and p are individually equal to or greater than 1 and r is equal to or greater than 0, $Z_1$, and/or $Z_2$, and/or $Z_3$, and/or $Z_4$, independently for each repetition unit n, p, and r, are selected from the group consisting of OH, alanine, and a compound according to Formula (II),

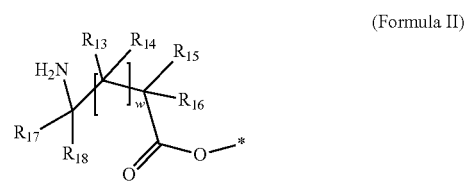

(Formula II)

wherein w is an integer in the range of from 1 to 4, wherein the compound according to Formula (II) connects to the compound according to Formula (I) via the bond labeled with *, with the proviso that at least one substituent $Z_1$, and/or $Z_2$, and/or $Z_3$, and/or $Z_4$, is not OH and with the proviso that wherein for n and p are individually equal to or greater than 1 and r is equal to or greater than 0, at least one unit $A_1$, $A_2$, or $A_3$ is selected from the group consisting of 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein the esteramine is obtained by the process comprising the steps of a) reacting an alcohol according to Formula (III)

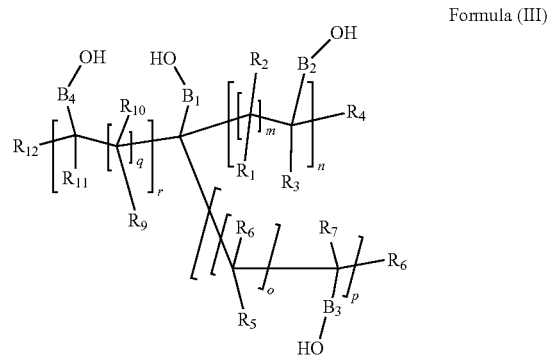

Formula (III)

wherein independently from each other n, m, p, o, r and q, are defined above;

$B_1$, $B_2$, $B_3$, $B_4$, $R_1$, $R_2$, $R_3$ $R_4$, $R_5$, $R_6$, $R_7$, $R_8$, $R_9$, $R_{10}$, $R_{11}$, and $R_{12}$ are defined above;

with one or more $C_2$ to $C_{16}$ alkylene oxide, followed by
b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

(Formula IV)

with w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl.

4. An esteramine of Formula (I) or salt thereof, (Formula I)

wherein independently from each other
n is 1;
m is 0;
p is 1;
o is 0;
r is 0;
q being an integer for each repetition unit r independently selected from 0 to 12;
s being an integer from 0 to 100;
t being an integer from 1 to 100;
u being an integer from 0 to 100;
v being an integer from 0 to 100;
$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;
$B_1$ is a chemical bond;

$B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;
$R_4$, $R_8$, and $R_{12}$ being selected from the group consisting of H, linear alkyl, branched alkyl, and cycloalkyl;
$R_1$ and $R_2$ being independently for each repetition unit m of each repetition unit n being selected from the group consisting of H, linear alkyl, branched alkyl, and cycloalkyl;
$R_5$ and $R_6$ being independently for each repetition unit o of each repetition unit p being selected from the group consisting of H, linear alkyl, branched alkyl, and cycloalkyl;
$R_9$, $R_{10}$, and $R_{11}$ being independently for each repetition unit q of each repetition unit r being selected from the group consisting of H, linear alkyl, branched alkyl, and cycloalkyl;
$R_3$, $R_4$, $R_7$, $R_8$, and $R_{12}$ are all equal to H; and
with the proviso that $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso that at least one substituent $Z_1$, and/or $Z_2$, and/or $Z_3$, and/or $Z_4$, is not OH, and wherein for n and p equal to 1 and r equal to 0 at least one unit $A_1$, $A_2$, or $A_3$ is selected from the group consisting of 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl; and
with the proviso that at least one substituent $Z_1$, and/or $Z_2$, and/or $Z_3$, and/or $Z_4$, is not OH, wherein the esteramine is obtained by the process comprising the steps of a) reacting an alcohol according to Formula (III)

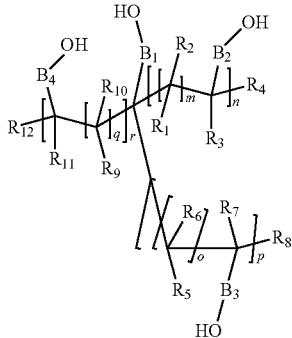

Formula (III)

wherein independently from each other n, m, p, o, r and q, are defined above;

$B_1, B_2, B_3, B_4, R_1, R_2, R_3, R_4, R_5, R_6, R_7, R_8, R_9, R_{10}, R_{11}$, and $R_{12}$ are defined above;

with one or more $C_2$ to $C_{16}$ alkylene oxide, followed by b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

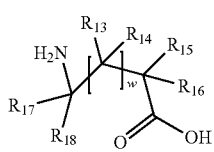

(Formula IV)

with w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

5. An esteramine of Formula (I) or salt thereof,

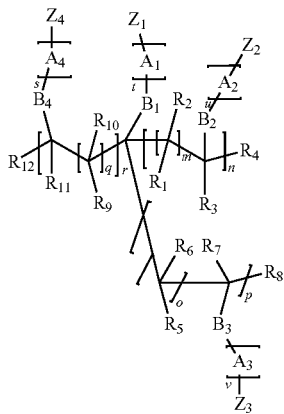

(Formula I)

wherein independently from each other n is 1;
m is 0;
p is 1;
o is 0;
r is 0;
q being an integer for each repetition unit r independently selected from 0 to 12;
s being an integer from 0 to 100;
t being an integer from 1 to 100;
u being an integer from 0 to 100;
v being an integer from 0 to 100;
$A_1, A_2, A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;
$B_1$ is a methylene;
$B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;
$R_1$ and $R_2$ being independently for each repetition unit m of each repetition unit n being selected from the group consisting of H, linear alkyl, branched alkyl, and cycloalkyl;
$R_5$ and $R_6$ being independently for each repetition unit o of each repetition unit p being selected from the group consisting of H, linear alkyl, branched alkyl, and cycloalkyl;
$R_9$, $R_{10}$, and $R_{11}$ being independently for each repetition unit q of each repetition unit r being selected from the group consisting of H, linear alkyl, branched alkyl, and cycloalkyl;
$R_3$, $R_4$, $R_7$, and $R_8$, are all equal to H;
$R_{12}$ is equal to ethyl; and
with the proviso that $Z_1$, and/or $Z_2$, and/or $Z_3$, and/or $Z_4$, independently for each repetition unit n, p, and r, are selected from the group consisting of OH, alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso that at least one substituent $Z_1$, and/or $Z_2$, and/or $Z_3$, and/or $Z_4$, is not OH, and wherein for n and p equal to 1 and r equal to 0 at least one unit $A_1$, $A_2$, or $A_3$ is selected from the group consisting of 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group and

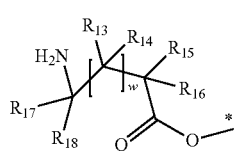

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl; and with the proviso that at least one substituent $Z_1$, and/or $Z_2$, and/or $Z_3$, and/or $Z_4$, is not OH, wherein the esteramine is obtained by the process comprising the steps of a) reacting an alcohol according to Formula (III)

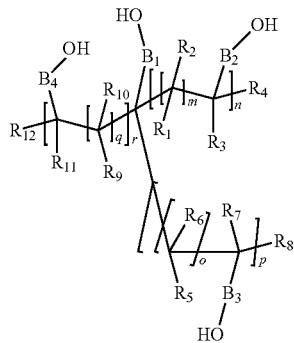

Formula (III)

wherein independently from each other n, m, p, o, r and q, are defined above;

$B_1$, $B_2$, $B_3$, $B_4$, $R_1$, $R_2$, $R_3$, $R_4$, $R_5$, $R_6$, $R_7$, $R_8$, $R_9$, $R_{10}$, $R_{11}$, and $R_{12}$ are defined above;

with one or more $C_2$ to $C_{16}$ alkylene oxide, followed by b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof;

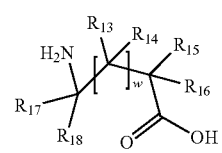

(Formula IV)

with w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

6. An esteramine of Formula (I) or salt thereof,

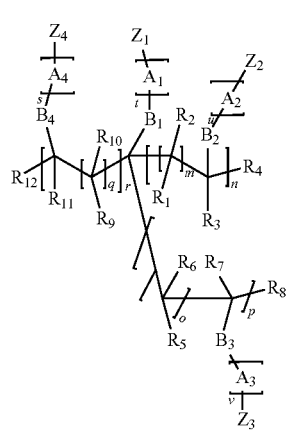

(Formula I)

wherein independently from each other n being an integer from 1 to 12;

m being an integer for each repetition unit n independently selected from 0 to 12;

p is 0;

o being an integer for each repetition unit p independently selected from 0 to 12;

r is 0;

q being an integer for each repetition unit r independently selected from 0 to 12;

s being an integer from 0 to 100;

t being an integer from 1 to 100;

u being an integer from 0 to 100;

v being an integer from 0 to 100;

$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;

$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the proviso that when p and r are both equal to 0, and n being at least 1, $Z_1$ and $Z_2$, are independently selected from the group consisting of OH and lysine, with the proviso that at least one substituent $Z_1$ and/or $Z_2$ is not OH, and with the proviso that $R_3$ contains equal to or more than 2 carbon atoms.

7. An esteramine of Formula (I) or salt thereof,

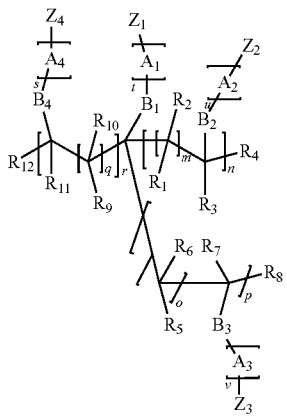

(Formula I)

wherein independently from each other
n being an integer from 1 to 12;
m being an integer for each repetition unit n independently selected from 0 to 12;
p is 0;
o being an integer for each repetition unit p independently selected from 0 to 12;
r is 0;
q being an integer for each repetition unit r independently selected from 0 to 12;
s being an integer from 0 to 100;
t being an integer from 1 to 100;
u being an integer from 0 to 100;
v being an integer from 0 to 100;
$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;
$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;
$R_4$, $R_8$, and $R_{12}$ being selected from the group consisting of H, linear alkyl, branched alkyl, and cycloalkyl;
$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the proviso that when p and r are both equal to 0, and n being at least 1, $Z_1$ and $Z_2$, are independently selected from the group consisting of OH and alanine, with the proviso that at least one substituent $Z_1$ and/or $Z_2$ is not OH, and with the proviso that $R_3$ contains equal to or more than 2 carbon atoms.

8. An esteramine of Formula (I) or salt thereof,

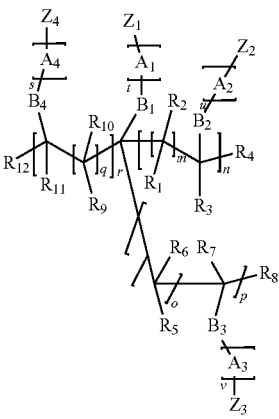

(Formula I)

wherein independently from each other
n being an integer from 1 to 12;
m being an integer for each repetition unit n independently selected from 0 to 12;
p is 0;
o being an integer for each repetition unit p independently selected from 0 to 12;
r is 0;
q being an integer for each repetition unit r independently selected from 0 to 12;
s being an integer from 0 to 100;
t being an integer from 1 to 100;
u being an integer from 0 to 100;
v being an integer from 0 to 100;
$A_1$, $A_2$, $A_3$, and $A_4$ are independently from each other and independently for each repetition unit s, t, u, or v, selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group;
$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;
$R_4$, $R_8$, and $R_{12}$ being selected from the group consisting of H, linear alkyl, branched alkyl, and cycloalkyl;
$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the proviso that when p and r are both equal to 0, and n being at least 1, $Z_1$ and $Z_2$, are independently selected from the group consisting of OH and glycine, with the proviso that at least one substituent $Z_1$ and/or $Z_2$ is not OH, and with the proviso that $R_3$ contains equal to or more than 2 carbon atoms.

9. An esteramine of Formula (I) or salt thereof,

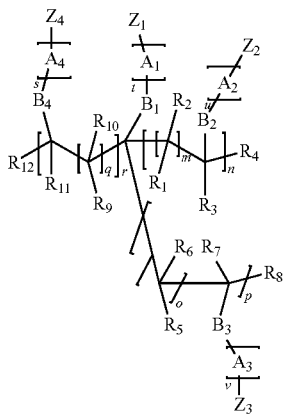

(Formula I)

wherein independently from each other n being an integer from 1 to 12;

m being an integer for each repetition unit n independently selected from 0 to 12;

p is 0;

o being an integer for each repetition unit p independently selected from 0 to 12;

r is 0;

q being an integer for each repetition unit r independently selected from 0 to 12;

s being an integer from 0 to 100;

t being an integer from 1 to 100;

u being an integer from 0 to 100;

v being an integer from 0 to 100;

$A_1$, $A_2$, $A_3$, and $A_4$ are independently from each other and independently for each repetition unit s, t, u, or v, selected from the list consisting of ethyleneoxy group;

$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the proviso that when p and r are both equal to 0, and n being at least 1, $Z_1$ and $Z_2$, are independently selected from the group consisting of OH, alanine, glycine, lysine, and a compound according to Formula (II), wherein said compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms;

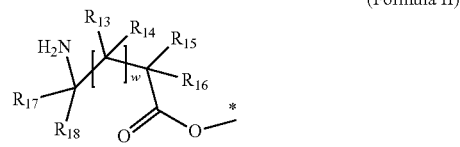

(Formula II)

with independently from each other w being an integer from 1 to 4;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

10. An esteramine of Formula (I) or salt thereof,

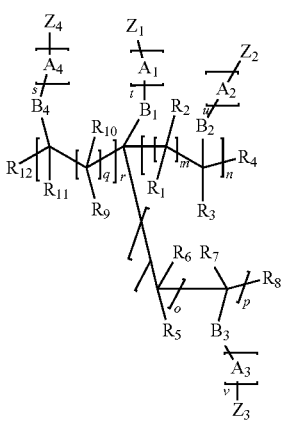

(Formula I)

wherein independently from each other n being an integer from 1 to 12;

m being an integer for each repetition unit n independently selected from 0 to 12;

p is 0;

o being an integer for each repetition unit p independently selected from 0 to 12;

r is 0;

q being an integer for each repetition unit r independently selected from 0 to 12;

s being an integer from 0 to 100;

t being an integer from 1 to 100;

u being an integer from 0 to 100;

v being an integer from 0 to 100;

$A_1$, $A_2$, $A_3$, and $A_4$ are 1,2-propyleneoxy group;

$B_1$, $B_2$, $B_3$, and $B_4$, are independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$R_1$, $R_2$, and $R_3$ being independently for each repetition unit m of each repetition unit n being selected from the group consisting of H, linear alkyl, branched alkyl, and cycloalkyl;

$R_5$, $R_6$, and $R_7$ being independently for each repetition unit o of each repetition unit p being selected from the group consisting of H, linear alkyl, branched alkyl, and cycloalkyl;

$R_9$, $R_{10}$, and $R_{11}$ being independently for each repetition unit q of each repetition unit r being selected from the group consisting of H, linear alkyl, branched alkyl, and cycloalkyl;

i) with the proviso that when p and r are both equal to 0, and n being at least 1, $Z_1$ and $Z_2$, are independently selected from the group consisting of OH, alanine, glycine, lysine, and a compound according to Formula (II), wherein said compound according to Formula (II) connects to the compound according to Formula (I) via the bond labeled with *, with the proviso that at least one substituent $Z_1$ and/or $Z_2$ is not OH, and with the proviso that $R_3$ contains equal to or more than 2 carbon atoms;

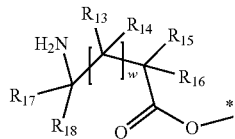

(Formula II)

with independently from each other w being an integer from 1 to 4;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

* * * * *